US008777894B2

(12) United States Patent
Butterfield et al.

(10) Patent No.: US 8,777,894 B2
(45) Date of Patent: *Jul. 15, 2014

(54) INFUSION DATA COMMUNICATION SYSTEM

(75) Inventors: Robert D. Butterfield, Poway, CA (US); David L. Schlotterbeck, Laguna Niguel, CA (US)

(73) Assignee: CareFusion 303, Inc., San Diego, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/291,008

(22) Filed: Nov. 7, 2011

(65) Prior Publication Data

US 2012/0053533 A1  Mar. 1, 2012

Related U.S. Application Data

(63) Continuation of application No. 10/812,723, filed on Mar. 29, 2004, now Pat. No. 8,075,514.

(60) Provisional application No. 60/458,311, filed on Mar. 28, 2003.

(51) Int. Cl.
 *A61M 31/00* (2006.01)

(52) U.S. Cl.
 USPC .......................................................... 604/65

(58) Field of Classification Search
 USPC ............ 604/890.1, 891.1, 131, 65–67; 710/8; 128/DIG. 12, DIG. 13
 See application file for complete search history.

(56) References Cited

U.S. PATENT DOCUMENTS

| 4,191,184 A * | 3/1980 | Carlisle .......................... 604/153 |
| 6,989,755 B2 * | 1/2006 | Matsushita et al. ........... 340/603 |
| 8,075,514 B2 * | 12/2011 | Butterfield et al. ............. 604/65 |
| 2002/0038392 A1 * | 3/2002 | De La Huerga .................. 710/8 |

FOREIGN PATENT DOCUMENTS

| EP | 1274187 A1 | 1/2003 |
| EP | 1609106 A2 | 12/2005 |
| WO | WO-99/29356 A1 | 6/1999 |

OTHER PUBLICATIONS

WO 02/069530 A1, Matsushita, publication date=2002.*

* cited by examiner

*Primary Examiner* — Manuel Mendez
(74) *Attorney, Agent, or Firm* — McDermott Will & Emery LLP

(57) ABSTRACT

An infusion data communication system provides a communication link among a fluid container, an infusion pump, and a patient through which identification data may be communicated. Data devices are located at the fluid container and the patient and conduct low frequency RF energy at a low power level containing the data into the medical fluid. The data-laden RF energy propagates through the medication fluid to data readers at the infusion pump which receives the RF energy and reads the data. A comparison is made to verify that the right medication is mounted to the infusion pump for administration to the right patient. RFID devices may be used for the data devices and readers. Pump programming data may also be propagated to the infusion pump from the container RFID tag. The RFID device at the patient may be writable and may be used to store a patient MAR.

16 Claims, 5 Drawing Sheets

INFUSION DATA COMMUNICATION SYSTEM

CROSS-REFERENCES TO RELATED APPLICATIONS

This application is a continuation of application Ser. No. 10/812,723, filed on Mar. 29, 2004 and currently pending, which claims priority to provisional Application No. 60/458,311, filed Mar. 28, 2003, all of which are incorporated herein by reference.

BACKGROUND OF THE INVENTION

The present invention is generally related to fluid infusion, and more particularly, to a communication system and method for use in identification before the delivery of intravenous fluids.

Physicians and other medical personnel apply intravenous ("IV") infusion therapy to treat various medical complications in patients. IV infusion therapy typically involves infusing medical fluids, such as medications, drugs, or nutrients, from a fluid supply or container, such as a bag or bottle, through the tube of a fluid administration set to a cannula inserted into a patient's blood vessel.

In a typical facility, a physician enters an order for medication for a particular patient. This order may be handled either as a simple prescription slip, or it may be entered into an automated system, such as a physician order entry ("POE") system. The prescription slip or the electronic prescription from the POE system is routed to the pharmacy where the order is filled. Typically, the prescribed medication is prepared by a pharmacist and added to a bag or bottle at a pharmacy. A pharmacist also typically identifies the contents of the bag and the patient for whom the bag is intended with a paper label that is attached to the bag and in some cases by other means, such as, for example, a bar code or magnetic device, or by use of a radio frequency ("RF") signal interactive device such as a radio frequency identification device ("RFID") tag. The prepared medication is then delivered to a nurse's station for administration to the patient.

For safety reasons and in order to achieve optimal results, the medical fluid is often administered over a period of time in accurate amounts as prescribed by the physician and in a controlled fashion by using an infusion pump. Infusion pumps operate by displacing the fluid in the tube of a fluid administration set to move fluid from the fluid container through the tube and into the patient. The infusion pump is programmed by an operator such as a nurse or other medical personnel, with operating parameters to achieve the administration of the medication as prescribed by the physician. Such operating, or pumping, parameters are medication and patient specific. That is, the pumping parameters are selected based on the particular medication prescribed and the specific patient for whom they are intended. It is the nurse's responsibility to match the prescribed medication with the correct patient and with the properly programmed pump.

Hospitals and other institutions continually strive to provide quality patent care. Medical errors, such as when a patient receives the wrong medication or receives the correct medication at the wrong time or in the wrong dosage, are significant problems for all health care facilities. In the administration of medication, focus is typically directed to the following five "rights" or factors: the right patient, the right drug, the right route, the right amount, and the right time. The nurse aims to ensure that these "rights" are accomplished. Systems and methods seeking to reduce medical errors should also take these five "rights" into consideration.

Medical infusion pumps have advanced greatly over the years and permit more precise infusion control resulting in much better treatment for patients. Doctors are more assured that the quantities and rates of medication that they prescribe for their patients can be delivered to the patients accurately by infusion pumps. However, there remains a continuing concern that the right drug is matched to the right pump, and that the operating parameters (concentration, schedule, etc.) are correctly programmed into the right pump.

In some cases, a single patient may be prescribed multiple simultaneous infusions of different medications, sometimes four or more, which requires multiple infusion pumps that typically are programmed differently. In such cases, there will also be multiple administration sets each with its own fluid conduit or tube to be connected with the patient. Where there are multiple infusion conduits present, there is a concern that a fluid conduit may be mounted to the wrong infusion pump and the associated medication delivered under incorrect pumping parameters. As an example, where multiple infusion pumps are located side by side, or above and below each other, or where a multi-channel pump is used, the multiple fluid sources may be suspended immediately above each pump or pump channel and may become intertwined, thus making it difficult to select the correct fluid conduit for the particular pump or channel. Where a more dense infusion pump environment exists, it is important to be sure that the correct medical fluid conduits are being mounted to the correct pump or channel.

Prior attempts have been made to assure that the right medication is administered to the right patient through the right pump. Patient identification, medical fluid identification, infusion pump identification, and caregiver identification have been achieved electronically through the use of bar code tags, in some cases RFID ("Radio Frequency IDentification") tags or devices, and by other means. In these systems, an operator such as a nurse uses a bar code or RFID reader connected to the pump to read the tags to automatically program the pump and to verify that the medical fluid identification matches the patient identification.

Even though the foregoing have provided significant advances in the art to avoid medication errors and have reduced the likelihood of medication errors, there still exists some risk that an incorrect fluid container may become mounted to a pump or pump channel. Stated differently, there still exists some risk that a fluid container may become connected to the wrong pump or pump channel. For example, the nurse could possibly scan the tag of the correct container, but become distracted and mount the conduit of the administration set connected to the container to the wrong pump channel. Even if the nurse does not become distracted, the various fluid conduits in a multiple fluid infusion may be difficult to distinguish from one another and tracing the fluid conduit associated with the right container may become burdensome, especially where the fluid conduits have become tangled with each other. In such a case, the nurse may inadvertently choose the wrong fluid conduit to install in the pump even after identifying the correct fluid container.

In one attempt to correctly link the fluid conduit with the right pump, a data bus composed of wires is embedded in or attached to an IV line for linking a tag reader located adjacent an IV bag's information tag to a data port of a pump unit. However, this system does not provide a communication path that includes a link between the patient identification tag and the pump unit to be sure that the bag is connected to the right patient. It would be advantageous to provide a system that includes a complete communication path between the patient, the pump, and the fluid container. It would also be advantageous to provide a system that does not require the use of additional equipment such as wires and connectors that must be assembled together or a separate tag reader that must be located adjacent an information tag to provide a communication path. Nurses are quite busy already and adding the duty of connecting wires together would make their jobs even busier.

Additionally, some record-keeping systems in healthcare facilities do not provide for instantaneous update of a patient's medication administration record ("MAR") when an infusion has been administered. Consequently, there exists the possibility that a healthcare worker may believe that the patient has not received his or her infusion and give the infusion a second time. Therefore, it would also be advantageous to provide a system that captures infusion information and automatically updates the patient's medication administration record.

Hence, those skilled in the art have recognized that a need still exists for a system and method to more accurately ensure that the correct fluids are infused into the patient at the correct pumping parameters. In particular, it would be desirable to have a system and method that provide for accurate and efficient communication between a medical fluid container, an infusion pump, and a patient for verifying that the right medication is delivered to the right patient at the right operating parameters. A further need has been recognized for a system and method that automatically updates the patient's medication administration record. The present invention fulfills these needs and others.

INVENTION SUMMARY

Briefly, and in general terms, the present invention is directed to a communication system and method for use in the delivery of intravenous fluids. An infusion data communication system having a communication link with which relevant administration data may be communicated in a medical fluid administration system is provided, the administration system comprising a medical fluid container at an upstream end, a patient at a downstream end, and a conduit connected to both the container and the patient, through which medical fluid from the container is conducted toward the patient for administration. The infusion data communication system comprises a first data transmitting device located at either the medical fluid container or the patient, the first data transmitting device configured to transmit relevant administration data into medical fluid residing at its location, the conduit having a lumen containing the medical fluid to be infused to the patient, and a first data reader device located at the conduit at a location between the upstream end and the downstream end of the conduit, the first data reader device configured to receive from the medical fluid in the lumen the relevant administration data transmitted into the medical fluid by the first data transmitting device.

In more detailed aspects, the first data transmitting device is disposed at the medical fluid container and comprises an RFID transponder, and the first data reader device comprises an RFID reader. Further, the first data transmitting device located at the medical fluid container is configured to transmit the relevant administration data into the medical fluid at a frequency and a power level selected such that the data will remain substantially within the lumen of the conduit.

In yet other aspects, the conduit comprises a drip chamber that is conductive to the relevant administration data. Further, the conduit is coupled downstream to an infusion pump and the first data reader device is located at the infusion pump.

The relevant administration data comprises drug identification data, patient identification data, and infusion parameter data.

In further aspects, the infusion data communication system further comprises a second data transmitting device located at the patient, the second data transmitting device configured to transmit relevant patient data into medical fluid residing in the fluid conduit attached to the patient, and a second data reader device located at the conduit at a location upstream from the patient, the second data reader device configured to receive from the medical fluid the relevant patient data transmitted into the medical fluid by the second data transmitting device. The relevant patient data from the second data transmitting device comprises patient identification data. Additionally, the conduit is coupled upstream to the infusion pump and the second data reader device is located at the infusion pump. A processor compares the patient identification data from the relevant administration data to the patient identification data from the relevant patient data and provides an alert if the two patient identification data do not match.

In other more detailed aspects of the invention, the relevant patient data of the second data transmitting device also comprises a medical administration record of the patient. The second data transmitting device at the patient comprises an RFID transponder, and the RFID transponder at the patient is writable. Additionally, the second data reader device located upstream of the patient comprises a second RFID reader which is configured to also transmit patient medication administration record data into the fluid in the lumen of the tube. The processor is configured to transmit with the second data reader/writer device data regarding the current administration of medication into the medical fluid in the lumen, the second data transmitting device being also writable and being configured to receive the current administration data from the medical fluid and write such received data into the second data transmitting device at the patient.

These and other advantages of the invention will become apparent from the following more detailed description when taken in conjunction with the accompanying drawings of illustrative embodiments.

BRIEF DESCRIPTION OF THE DRAWINGS

FIG. 3 is a perspective view of one of the fluid infusion pumps of FIGS. 1 and 2 with its front door in the open position showing two RFID readers used in accordance with aspects of the present invention, a peristaltic four finger pump mechanism, and a fluid conduit in operative engagement with the infusion pump;

DETAILED DESCRIPTION OF THE PREFERRED EMBODIMENTS

In accordance with aspects of the invention, there is provided a unique communication system and method that automatically ensure that the proper medication and dosage are delivered to the patient for whom that medication and dosage are intended. An information communication network is provided that uses the IV fluid and the patient's body as carriers of low power radio frequency ("RF") signals. The infusion pump receives these signals from the IV fluid allowing identification of the patient and the medical fluid container and in some cases allows pump programming to be automatically accomplished, thus reducing the number of manual operations required of the caregiver.

Figure 1:
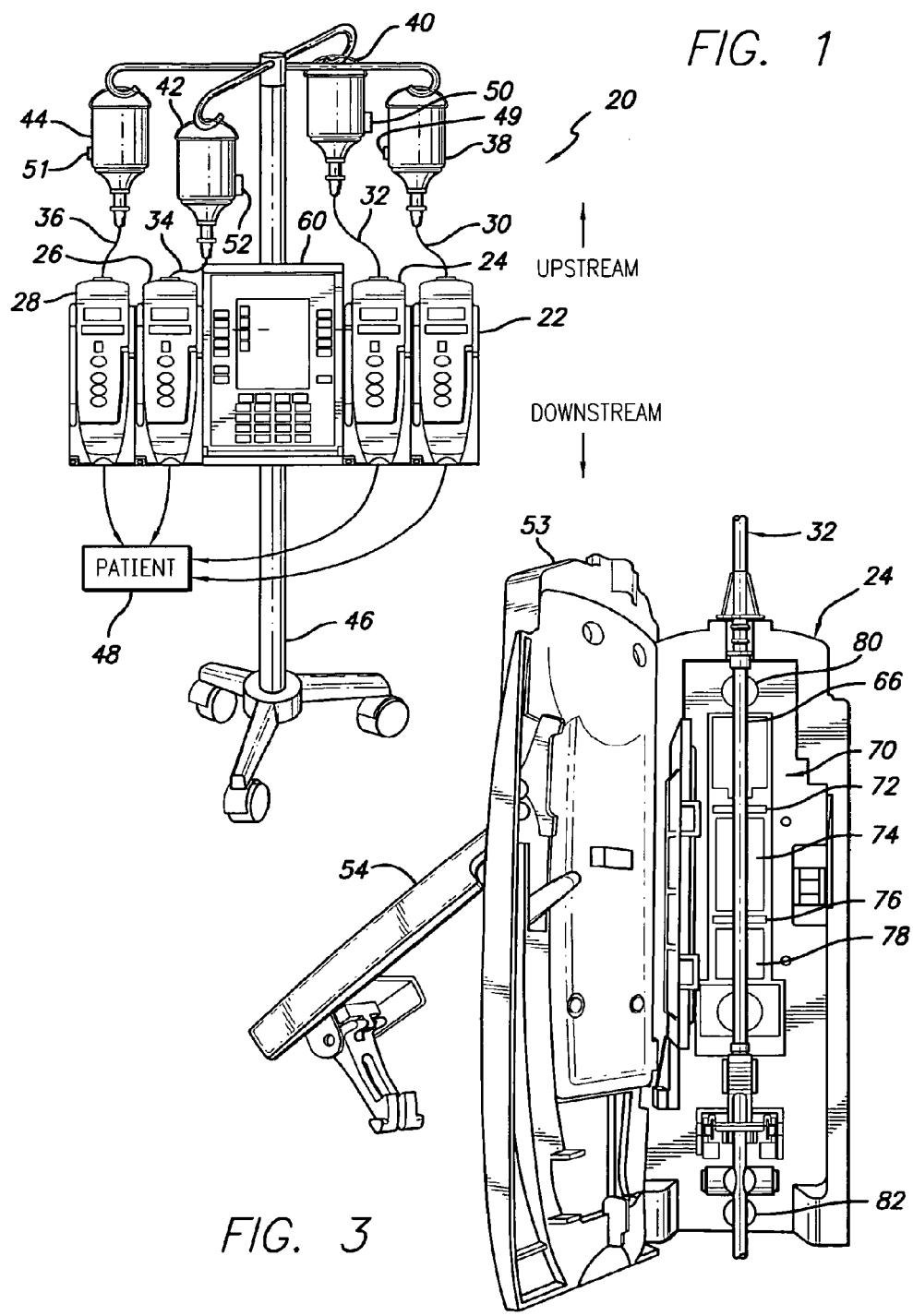
FIG. 1 is a front view of a medical administration system having four fluid infusion pumps, each of which is connected to a respective fluid container for pumping the contents of the fluid container to a patient, the fluid containers being mounted on a common roller stand.

Referring now in more detail to the drawings in which like reference numerals refer to like or corresponding elements among the several views, there is shown in FIG. 1 a medical administration system 20 having four medical administration devices 22, 24, 26, and 28, which are infusion pumps in this embodiment, each of which is in operative engagement with a respective fluid administration set 30, 32, 34, and 36. Medical fluid supplies or containers 38, 40, 42, and 44, which may take various forms but in this case are shown as inverted bottles, are suspended above the pumps. Fluid supplies may also take the form of bags or other types of containers. Both the infusion pumps 22, 24, 26 and 28 and the fluid containers 38, 40, 42, and 44 are mounted to a roller stand or IV pole 46.

Each administration set 30, 32, 34, and 36 is connected between a respective fluid container 38, 40, 42, and 44 and the same patient 48 so that the patient may receive the fluids in all four fluid containers. A separate infusion pump 22, 24, 26, and 28 is used to infuse each of the fluids of the fluid containers into the patient. The infusion pumps are flow control devices that will act on the respective tube or fluid conduit of the fluid administration set to move the fluid from the fluid container through the conduit to the patient. Because individual pumps are used, each can be individually set to the pumping or operating parameters required for infusing the particular medical fluid from the respective fluid container into the patient at the particular rate prescribed for that fluid by the physician. Such medical fluids may comprise medications, drugs, nutrients, or other therapeutic fluids as previously mentioned.

Typically, medical fluid administration sets have more parts than those shown in FIG. 1. Many have check valves, drip chambers, valved ports, connectors, and other devices well known to those skilled in the art. Except for FIG. 4 where a drip chamber is shown as part of the administration set, these other devices have not been included in the drawings so as to preserve clarity of illustration. However, those skilled in the art will understand that the inclusion of such other devices may often occur.

In accordance with the background discussed above, it is desirable to verify that each fluid container 38, 40, 42 and 44 is associated with the correct patient 48, that the pumping parameters for a given medical fluid have been correctly programmed into the infusion pump 22, 24, 26 or 28, and that each fluid container is correctly connected to the appropriately programmed pump. As will be discussed in more detail below, the present invention provides a communication link between the patient and each pump, and between each medical fluid container and each pump. Using these communication links, data devices associated with the medical fluid containers, such as data transmitting devices 49, 50 51, and 52 shown mounted on the bottles, or a data transmitting device 92 (shown in FIG. 4) associated with the patient 48, may communicate relevant administration data to the pumps for verifying that the medical administration system 20 has been connected correctly. Relevant administration data may include various data related to the administration of medical fluid to a particular patient. For example, relevant administration data may include drug identification, patient identification, and other information believed to be relevant.

It should be noted that the drawing of FIG. 1 is not to scale and that distances have been compressed and sizes have been exaggerated for the purpose of clarity. In an actual setting, the distance between the containers 38, 40, 42, and 44 and the infusion pump 22, 24, 26, and 28 could be much greater. There would be more of an opportunity for the tubes of the administration sets 30, 32, 34, and 36 to become intertwined with each other when all four are dangling from the containers, which can cause confusion as to which tube should be in which infusion pump. The opportunity for confusion increases as the number of tubes increases. However, it should also be understood that the present invention is also useful in cases where a single pump and single medical fluid container are involved, as the system may also be used to confirm that the correct medication has arrived for the patient and that the infusion parameters have been correctly programmed into the pump.

Figure 2:
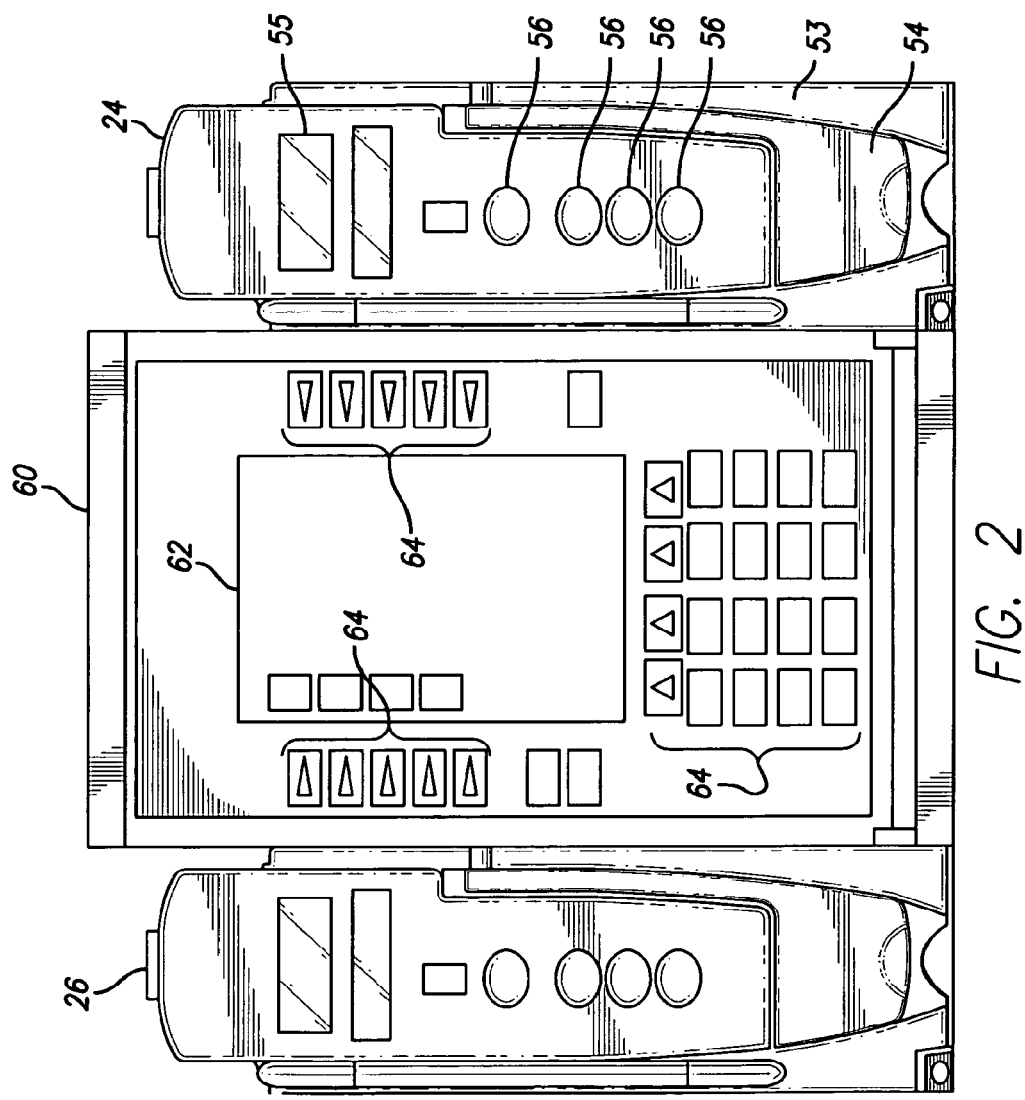
FIG. 2 is an enlarged view of a portion of the medical administration system of FIG. 1 showing two of the fluid infusion pumps mounted at either side of a programming module, and the displays and control keys of each, with the programming module being capable of programming both infusion pumps.

Referring now to FIG. 2, an enlarged view of the front of the infusion pump 24 is shown. The pump includes a front door 53 and a handle 54 that operates to lock the door in a closed position for operation and to unlock and open the door for access to the internal pumping and sensing mechanisms and to load administration sets for the pump. When the door is open, the tube can be connected with the pump, as will be shown in FIG. 3. When the door is closed, the tube is brought into operating engagement with the pumping mechanism and the other equipment of the pump. A display 55, such as an LED display, is located in plain view on the door in this embodiment and may be used to visually communicate various information relevant to the pump, such as alert indications (e.g., alarm messages). Control keys 56 exist for programming and controlling operations of the infusion pump as desired. The infusion pump 24 also includes audio alarm equipment in the form of a speaker 58 (shown in FIG. 5).

In the embodiment shown in FIG. 2, the infusion pump 24 is attached to the right side a programming module 60. Other devices or modules, including another infusion pump, may be attached to the right side of the infusion pump 24, as shown in FIG. 1. In such a system, each attached pump represents a pump channel of the overall medical administration system 20. In one embodiment, the programming module is used to provide an interface between the infusion pump 24 and external devices as well as to provide most of the operator interface for the infusion pump 24. Attention is directed to U.S. Pat. No. 5,713,856 entitled "Modular Patient Care System" to Eggers et al., incorporated herein by reference, in which the programming module is described as an advanced interface unit. In other cases, the programming module is referred to as a "point-of-care unit."

The programming module 60 includes a display 62 for visually communicating various information, such as the operating parameters of the pump 24 and alert indications and alarm messages. The programming module 60 may also include a speaker (not shown) to provide audible alarms. The programming module also has various input devices in this embodiment, including control keys 64. The programming module also has a communications system (not shown) with which it may communicate with external equipment such as a medical facility server or other computer and with a portable processor, such as a handheld portable digital assistant ("PDA"), or a laptop-type of computer, or other information device that a caregiver may have to transfer information as well as to download drug or medication libraries to a programming module or pump. The communications system may take the form of a RF system, an optical system such as infrared, a Blue Tooth system, or other wired or wireless system. The communications system may alternatively be included integrally with an infusion pump, such as in cases where it is a stand alone pump. Further, information input devices need not be hard-wired to medical instruments, information may be transferred through a wireless connection as well.

FIG. 2 includes a second pump module 26 connected to the programming module 60. As shown in FIG. 1, more pump modules may be connected. Additionally, other types of modules may be connected to the pump modules or to the programming module.

Turning now to FIG. 3, the infusion pump 24 is shown in perspective view with the front door 53 open, showing the administration set 32 in operative engagement with the pump 24. The fluid administration set 32 comprises a fluid conduit or tube 66, extending from the respective fluid container 40 (FIG. 1) to the patient 48, upon which the pump acts to move fluid downstream to the patient. Specifically, a pumping mechanism 70 acts as the flow control device of the pump to move fluid though the conduit. In this case, the pumping mechanism is of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid container to the patient. The operation of peristaltic pumps including four finger pumps is well known to those skilled in the art and no further operational details are provided here.

In this particular embodiment, the pump 24 also includes two data reader devices, upstream data reader device 80, and downstream data reader device 82, for receiving information relating to the infusions, such as drug identification, patient identification, and optionally other information such as nurse identification. The data reader devices may comprise RFID readers (or receivers) or other wireless devices that are compatible with the data transmitting devices 50 and 52 associated with the fluid containers 40 and 42 and the data transmitting device associated with the patient. Although referred to as data reader devices or RFID readers or receivers, the data reader devices may also transmit interrogation signals to the RFID transponder associated with the fluid container or the patient and as described below may also transmit data into the medical fluid in the tube lumen. Likewise, although referred to as data transmitting devices or RFID tags or RFID transponders, data transmitting devices may also receive or read data and may also re writable, as is discussed below in more detail. The readers 80 and 82 are operatively connected to the infusion pump and, in this embodiment, are further provided as an integral part of the pump 24. While the readers 80 and 82 may be located at a different location in the pump than shown in FIG. 3 or may even be a separate component in operative connection with the pump, the upstream data reader device 80 is generally located upstream from the pumping mechanism 70, that is, at a location between the fluid container 40 (FIG. 1) and the pumping mechanism. Likewise, the downstream data reader device 82 is generally located at a downstream location with respect to the pumping mechanism, i.e., between the pumping mechanism and the patient 48. In another embodiment, the pump 24 may include a single data device, either the upstream data reader device 80 or the downstream data reader device 82.

The terms "upstream" and "downstream" as shown in FIG. 1 and as used herein in various places is meant to provide an indication of relative positioning as well as indicate the positions of certain specific devices. For example, the patient is located "downstream" from the pump and is also "downstream" from the container. The pump is located "upstream" from the patient, as is the container. On the other hand, there is an "upstream data reader device" and a "downstream data reader device" which denote their relative positions on the pump.

As mentioned above, once the tubing 66 is engaged with the pumping mechanism 70 and the door 53 of the pump is closed, the pumping mechanism always provides an occlusion of the channel so that there is never an open fluid line from upstream of the pumping mechanism to downstream of the pumping mechanism. At the location of such an occlusion, any medical fluid carried by the tube is absent and therefore cannot provide a conductive path for energy introduced into the medical fluid by a data transmitting device 50 and 92, such as an RFID tag. This prevents low frequency RF signals that are being transmitted though the fluid in accordance with an aspect of the invention from traveling across the entire pumping mechanism. Thus, providing one reader upstream 80 and one reader downstream 82 from the pumping mechanism permits communication with signals from both segments of the fluid line.

The occlusion of the fluid line 66 provided by the pumping mechanism 70 is advantageous in that it reduces the opportunity for cross-talk between fluid container data via a common patient-side conductive path. It is not uncommon for a single pumping system to have multiple channels that are connected to the same patient. In such cases, it may be undesirable for data from one medical fluid container channel to be communicated to another channel due to the common connection with the same patient. Although other steps may be taken due to the design of RFID devices themselves to prevent cross-talk interference, such as their anti-collision logic systems, the occluding devices in a peristaltic pump can effectively interrupt the communication of low frequency RF signals from the fluid container to the patient, thereby adding even more to resistance against cross-talk.

In another embodiment, as mentioned above, there may be a single data reader device located at the pump 24 that is used to read both the data transmitting device 50 at the medical fluid container and the data transmitting device 92 at the patient 48. This may be useful in the case where only a single conduit is used to infuse medical fluid to the patient. In such case, there are no multiple fluid conduits connected to the same patient through which crosstalk may occur.

Figure 4:
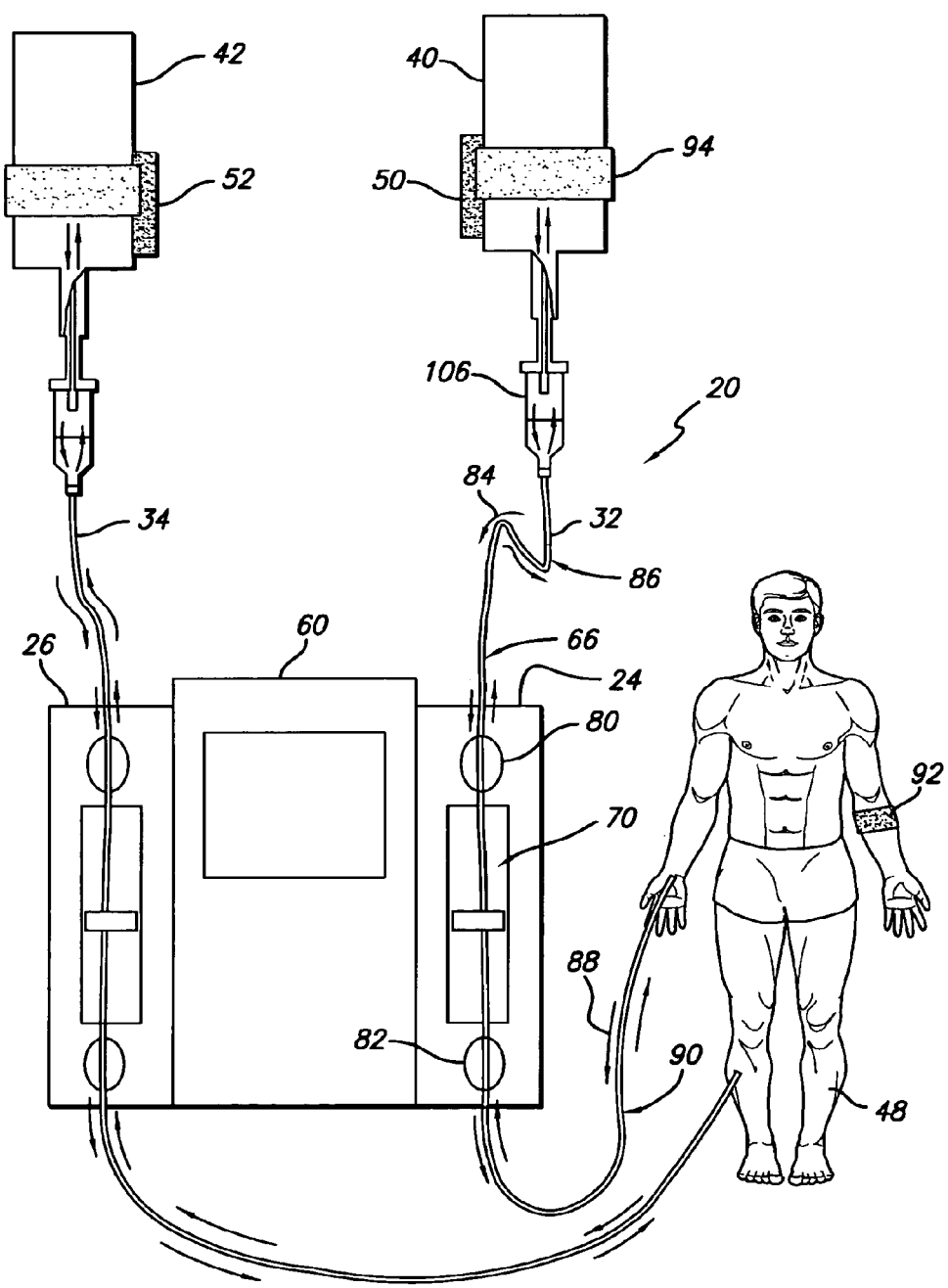
FIG. 4 is a schematic view of a communication system in accordance with aspects of the present invention, including the two infusion pumps from FIG. 2 operatively connected to medical fluid containers and to a patient for delivery of medical fluid and showing the communication paths used for communication between the medical fluid containers, infusion pumps, and patient.

FIG. 4 depicts a schematic view of the medical administration system 20 discussed above and an infusion data communication system in accordance with one embodiment of the present invention. An upstream communication path 84 is provided through the upstream portion 86 of the fluid conduit 66 which interconnects the fluid container 40 with the pump 24. More particularly, the upstream communication path 84 is provided via the medical fluid being moved from the container 40 through the conduit 66. A downstream communication path 88 is provided through the downstream portion 90 of the conduit 66 which interconnects the pump 24 with the patient 48, also via the medical fluid in the conduit 66. For illustrative purposes, the communication paths 84 and 88 between the infusion pump 24 and the medical fluid container 40 and the patient 48 are shown as arrows in FIG. 4. Such communication paths may be provided for each fluid line associated with the patient 48. Although the arrows are shown on either side of the fluid conduit 66 in FIG. 4 for clarity of illustration, it should be understood that the communication paths are actually provided through the fluid conduit 66 via the medical fluid.

The upstream communication path 84 links the data transmitting device 50 associated with the medical fluid container 40 to the upstream data reader device 80 of the pump 24, and the downstream communication path 88 links the data transmitting device 92 associated with the patient 48 to the downstream data reader device 82 of the pump 24.

In embodiments where the data reader devices 80 and 82 are RFID readers, the data transmitting 80 and 82 may comprise RFID transponders. In one embodiment, the relevant patient data transmitting device 92 is a patient information transmitter that may comprise an RFID tag that can also record information (i.e., is writable). The relevant patient data stored and transmitted by the RFID transponder 92 may include various information, for example, the patient's name, hospital identification number, and other information such as the patient's age, weight, condition, and allergies. In another embodiment, the patient's RFID transponder may also contain the patient's MAR (medication administration record) which the pump can update by writing information into its stored MAR data. Similarly, the fluid container RFID transponder 50 is a fluid identification transmitter that may also comprise an RFID tag. The container's RFID transponder 50 typically stores and transmits relevant administration data including patient identifiers such as numeric and alpha (name), a drug identifier, a drug concentration, a diluent fluid identifier, a dose or flow rate, other pumping-related parameters, and contra-indicated medications/conditions.

In one embodiment, the communication system of the present invention uses low power, low frequency RF signals for transmitting data via the communication paths 84 and 88. For example, the RF signals may have a frequency of about 100-300 kHz and a power of less than 100 nanowatts in this embodiment. It has been found that frequencies and power of this nature are conducted well enough by the ionic medical fluids yet are conducted poorly, if at all, by the material forming the wall of conduit 66 and air outside the conduit. These frequencies are not low enough to cause a muscle reaction in patients and are not high enough to radiate through tubing and through the ambient air. As a result, the communication energy used in the communication system in accordance with the invention is substantially confined by the wall of the tube 66. However, energy of other frequencies and power levels may function well also. Therefore, conduits that touch each other will not pass the data being conducted within the conduit to the touching conduit.

The transponders 50 and 92 may automatically and periodically transmit their information via the communication paths using the low frequency RF signals. The transponders 50 and 92 may be self powered or powered by an interrogation signal from an RFID reader 80 or 82 on the pump 24. As shown in FIG. 4 in exaggerated form, the transponders may each include an antenna 94 for receiving interrogation signals from a reader.

In one embodiment, the patient RFID transponder 92, which takes the form of a wristband in FIG. 4, is coupled to the downstream communication path 88 and to the RFID reader 82 via a further communication pathway through the patient 48. The RFID transponder 92 attached to the patient 48 may transmit the RF signals through the patient's body and through the medical fluid residing in the fluid conduit 66 attached to the patient, thereby providing communication with a medical administration device not directly attached to the body. The transmission of low range RF signals through the patient's body and through the fluid in the fluid conduit 66 provides a discrete communication path which avoids interference with the RF readers in adjacent pump channels.

Figure 5:
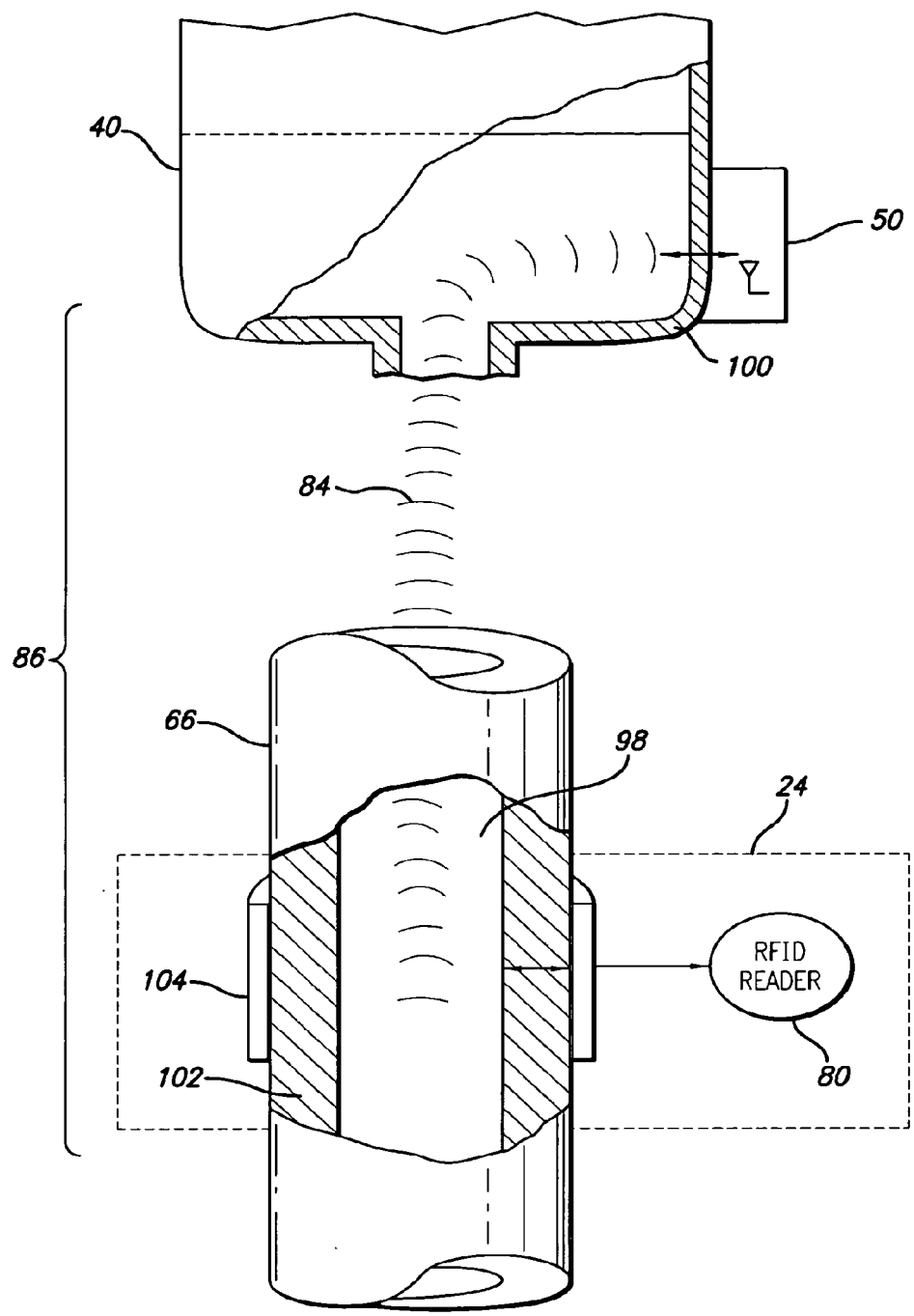
FIG. 5 is a more detailed view of one of the communication paths depicted in FIG. 4, showing the transmission of RF signals between the data device mounted to a medical fluid container and the data reader mounted to an infusion pump, including capacitive coupling through the container wall and the conduit wall.

When the fluid conduit 66 is mounted to the pump 24, the RFID readers 80 and 82 are placed into data communication with respective RFID transponders 50 and 92 via the communication paths 84 and 88 and receive signals being transmitted through the medical fluid residing in the respective conduit portions 86 and 90. FIG. 5 illustrates the transmission of RF signals along the upstream communication path 84. RF signals are transmitted into the medical fluid by the two RFID transponders 50 and 92. They propagate through the medical fluid in their respective fluid segments due to the ionic nature of that fluid. Those in the upstream portion 86 may be detected by the upstream reader 80 at the pump via capacitive coupling through the conduit wall 102, as shown in FIG. 5. RF signals in the downstream communication path 90 may similarly be transmitted through the conduit wall to the downstream reader 82.

In one embodiment, the pump 24 includes an electrically conductive device, such as metallized half-pipe 104, which is coupled to the RFID reader 80 to improve capacitive coupling through the conduit wall 102. The administration set 32 may also contain conductive devices to provide more efficient coupling with the pump's RFID readers. For example, a conductive device may be located in a fitment of the administration set 32 and may be configured to be mounted to a counterpart device in the pump 24, such as a half-pipe 104. For example, the conduit 66 may include a metallized or ceramic cylindrical insert that will be located adjacent the respective RFID reader 80 or 82 when the conduit 66 is properly loaded in the pump 24.

Similarly, the RFID transponder 50 mounted to the medical fluid container 40 is located and configured such that it may conduct RF signals to the fluid within the container via capacitive coupling through the container wall 100 in a way similar to that described above. The fluid container 40 may be fabricated to optimize the coupling of low frequency RF currents from the reader 50 into the medical fluid.

In another embodiment, fluid tubing formed of a more electrically conductive substance may facilitate the coupling between the RFID readers of the pump and the RFID transponders of the fluid container and patient, or may itself provide a suitable data signal conducting pathway. Other devices that may form a part of the administration set, such as a drip chamber 106 shown in FIG. 4, may also be formed of RF conductive material to improve the transmission of signals through the fluid line, particularly if the device may interrupt the fluid stream within the conduit. Such an interruption in the fluid pathway may be bridged by manufacturing the drip chamber from materials that are able to conduct the RF currents from the drip orifice at the upstream end of the drip chamber to the fluid in the drip chamber body. The improved RF conductivity may be provided by coatings and/or the embedding of conductive materials, such as carbon, within the drip chamber material or other molded component. Alternatively, a fiber material may be coated on the interior surface of the drip chamber to enable the medical fluid to maintain a fluid pathway through the drip chamber through a wicking effect.

Figure 6:
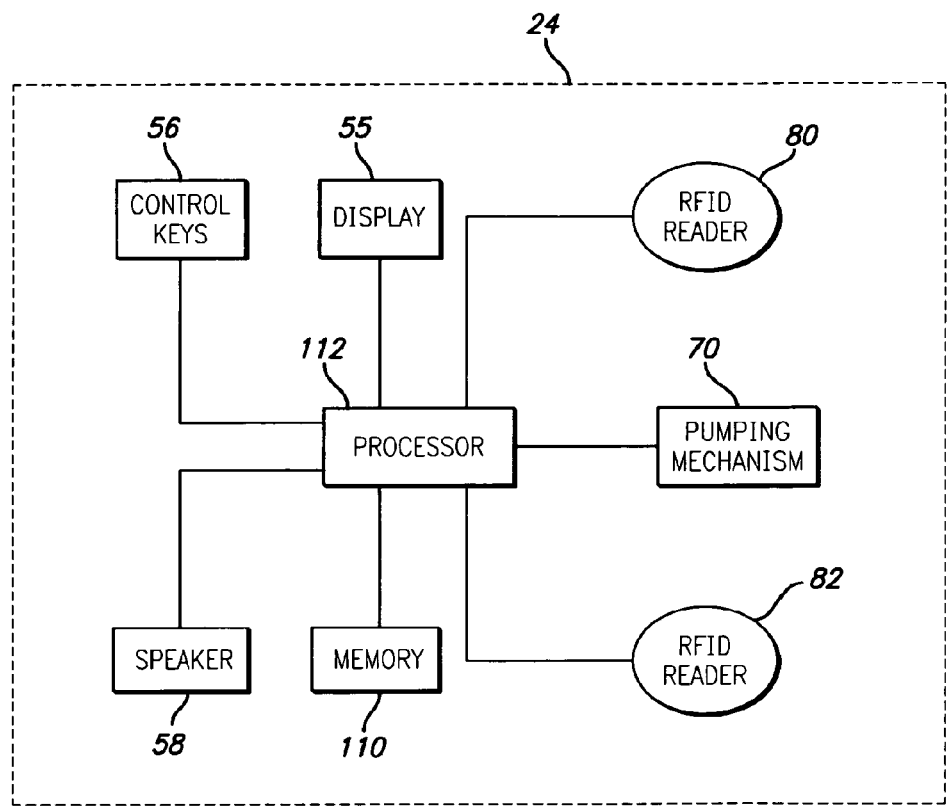
FIG. 6 shows a block diagram of the components of one of the infusion pumps from FIGS. 1 and 2.

Referring now to FIG. 6, the infusion pump's 24 RFID reader 80, which includes a decoder, converts the RF signals received from the fluid container transponder 50 (FIG. 4) into digital form. Similarly, the downstream reader 82 receives signals from the patient transponder 92 (FIG. 4) and converts them into digital form. The pump 24 includes a memory 110 for storing the received data and a processor 112 configured to analyze the data. Alternatively, the processor and the memory may be associated with the programming module 60 (FIG. 2) rather than the pump 24 in cases where a modular system is used. In another embodiment, the processor 112 and memory 110 may be located in a separate computer or workstation from the pump or programming module, or may even be located in a remote computer or server in communication with the pump or programming module via a wired or wireless network. As will be recognized by one skilled in the art, other arrangements are also possible.

In one embodiment, the processor 112 is configured to analyze the data received from the fluid container transponder 50 to determine if the correct fluid conduit has been loaded into the pump. For example, after a caregiver programs a pump by entering information such as drug identification and infusion parameters, the processor 112 may compare the entered drug identification with the drug identification transmitted by the fluid container transponder 50. If the drug identifications do not match, the processor 112 may activate an alarm to notify the caregiver of the discrepancy and will not permit the pump to begin the infusion until a response to the alarm has been received. The processor 112 may additionally check the entered infusion parameters with those transmitted by the fluid container transponder 50 to verify that this data matches as well. In the case of a modular infusion pump system, such as that shown in FIG. 1, where there is a single programming unit 60 that is used with multiple attached infusion pump modules 22, 24, 26, and 28, the programming unit 60 is used to program each of the infusion pump modules. The infusion pump modules may also be thought of as infusion "channels." The system and method in accordance with the invention is particularly useful in such a modular infusion system in that each infusion channel will have its own set of reader devices 80 and 82 (see FIG. 3). As the tube 66 for each container is installed in each infusion channel, the respective readers of that channel receive the data from the container attached to that tube. The programming unit will then receive the data from the channel and will compare that data to the programming instructions for that channel. If there is a discrepancy, the programming unit 60 will present an alarm.

As an example, if the programming unit 60 were used to program the infusion pump module 26 that is the second from the left in FIG. 1, "channel B," to infuse Dopamine, but the data from the upstream data reader 80 (FIG. 3) of channel B shows that the container attached to that tube contains Dextrose, the programming unit would provide an alert to the operator that the medication in channel B is incorrect. The programming unit would then not permit channel B to begin infusion until the discrepancy has been remedied. Further, if another channel attached to the programming unit, for example channel D (numeral 22), were programmed to administer Dextrose, the programming unit may also display the information that the tube that has been installed in channel B should instead be installed in channel D.

The processor 112 may also analyze the data by comparing the data from the patient transponder 92 to the data received from the fluid container transponder 50. The processor 112 verifies that the patient identification data received from the two sources matches to ensure that the correct medication is attached for the correct patient, and warns the caregiver through the operator interface of the infusion pump or other related device of any mismatch. Further, the infusion pump will not deliver fluid if a mismatch is detected. In the case of a mismatch, the processor may display an alert indication visually on the display 55 of the infusion pump 24 and/or an audible alarm from the speaker 58 of the pump (FIG. 2). The alert indication may also be provided on the display 62 and/or speaker of the programming module 60 (FIG. 2). In some embodiments, a record of the alert, together with related infusion data, may be stored in the memory 110 and/or communicated to a workstation, such as a nurse's station, the pharmacy, or a remote computer or server. In such cases, the record is available for further analysis and report generation.

If the wrong conduit 66 has been placed in the pump 24, the caregiver may reload the pump and attempt to program the pump again, with the verification process occurring again automatically. If the pump verifies that the patient identification data and fluid container transponders 92 and 50 match, a verification indication may be displayed on the displays 55 or 62 (FIG. 2) and the pump may permit the caregiver to continue programming the pump and/or begin the infusion. After programming of the pump is completed, the processor 112 will control the flow control device or pumping mechanism 70 to begin the infusion and move fluid through the fluid conduit 66 to the patient 48.

In one embodiment, the data transmitted from the fluid container transponder 50 may be used to automatically program the pump 24. The transmitted data, which may be stored in the memory 110 and accessed by the processor 112, may include the drug name and concentration, as well as various infusion parameters for the pump 24, such as dose or flow rate. The transmission of the fluid container data along the discrete communication path 84 ensures that the pump is receiving data associated with the fluid supply that is actually connected to the pump, thereby avoiding inadvertent loading of a different conduit in the pump. Once the medical fluid has been matched to the patient and the operating parameters have been transferred from the fluid container transponder 50 to the infusion pump, the caregiver may be prompted by the infusion pump to confirm the programmed data, including patient identification.

In one embodiment, the pump 24 may contain a drug library, which generally includes institutionally-established guidelines for administration of various medical fluids. For example, the drug library may include institutionally-established guidelines or limits on drug administration parameters, such as dosage, frequency of administration, and other delivery related information such as, for example, appropriate flow rates and infusion durations for programming infusion pumps. The drug library may be stored in the memory 110 of the pump 24 or in a memory of the programming module 60 (FIG. 2) or another memory connected to the pump 24 via a wired or wireless network. Other library storage arrangements are possible. Before the pump 24 is allowed to infuse a medical fluid into a patient, the processor 112 may be configured to check the operating parameters of the pump 24 against the drug library.

The drug library may contain "hard" and "soft" limit values on dosing parameters and other infusion parameters. Once the operating parameters have been programmed into the pump 24, the processor 112, according to its programming, will enter a verification stage in which it compares the programmed values against the stored library to verify that the programmed values are within acceptable ranges. If a programmed value contravenes a hard limit, the processor 112 may activate an alarm and require a value change before operation of the pump 24 can begin. If the programmed value contravenes a soft limit, the processor 112 may require an acknowledgment from the caregiver that he or she understands that the value entered is outside a soft limit but that this value is nevertheless to be used.

The drug library of the medical administration system may be configured to be periodically updated through the communications system using an external device such as a computer running appropriate software. Alternatively, the drug library may be stored on a remote computer or server in communication with the pump or programming module via a wired or wireless network.

The drug library may also include guidelines associated with patient-specific information that may be provided by the patient RFID transponder 92 attached to the patient 48. For example, in addition to storing patient identification data, the patient RFID transponder 92 may include patient characteristics, such as the patient's age, weight, medical conditions, allergies, and other known medical information. Information regarding the patient's medical history may also be stored in the patient RFID transponder 92. In one embodiment, the patient RFID transponder 92 contains the patient's MAR. These patient characteristics may be transmitted to the infusion pump 24 for comparison with the guidelines of the drug library in order to increase the safety and efficacy of the infusion program. In particular, the drug library may contain guidelines or limits for the administration of certain medical fluids based on particular patient characteristics, such as allergies, weight, age, medical condition, and other data.

In embodiments where the patient's MAR is stored in the patient RFID transponder 92, the processor 112 of the infusion pump 24 may be configured to check the patient's MAR stored on the RFID transponder 92 for any allergies of the patient, for other drug treatments (such as prior or concurrently scheduled infusions) that may provide a contra-indication to the present infusion, and for other medically-significant information. In one embodiment, the processor 112 of the infusion pump 24, or a processor of another monitor or module in communication with the infusion pump 24, may be programmed to read the patient's RFID transponder 92 and present that information on a display. For example, the pump 24 may contain a "patient MAR monitor" mode in which the contents of the patient's MAR retrieved from the patient transponder 92 may be displayed on display 55 or 62 (FIG. 2) and may be queried for certain information.

If the patient transponder 92 is a writable device, such as a writable RFID tag, the infusion pump 24 may additionally write information about the present infusion into the patient's MAR stored on the transponder 92. The transponder 92 attached to patient 48 may accordingly contain up-to-date information in the MAR to further ensure proper treatment at the hospital. For example, where the drug library resident in the pump includes guidelines for certain infusions based on other prior or concurrent infusions, the patient transponder 92 may provide the pump 24 with the patient's updated medical history for comparison with the guidelines. In accordance with healthcare facility procedures, the MAR in the patient's RFID transponder 92 may also be coupled to a healthcare facility server through other communication means, such as, for example, a wired or wireless network or a combination of wired and wireless communication channels, so that there is a backup copy of the MAR.

One particular mode of operation of the present invention will now be described. A patient 48 entering a hospital or other care-giving facility is provided with a wristband, necklace, ankle band or other identifier that is affixed to the patient in a manner so that the patient can be identified even if the patient is unconscious or otherwise unresponsive. This wristband or other device may include a data transmitting device, such as an RFID transponder 92, containing data representing the patient's name, hospital identification number, and other information that the facility has determined is important. Additional information such as the patient's age, weight, condition, allergies, and other known medical information may also be programmed into the device. In one embodiment, the patient's MAR is also programmed into the transponder. Periodically, the transponder will transmit this information through the patient's body using extremely low amplitude, low frequency, RF currents. In one embodiment as stated above, the RF signals have a frequency of about 100-300 kHz and a power of less than 100 nanowatts.

After the patient is admitted and situated in a bed within the facility, the patient is typically evaluated by a physician and a course of treatment is prescribed. The physician prescribes a course of treatment by preparing an order which may request a series of laboratory tests or administration of a particular medication to the patient. In some cases, the physician prepares the order by filling in a form or writing the order on a slip of paper to be entered into the hospital system for providing care. In other cases, the physician may enter the medication order directly into a physician order entry system or may instruct a nurse or other care-giving professional to do so.

If the order is for administration of a particular medication regimen, the order will be transmitted to the facility's pharmacy. The order will arrive in written or electronic form at the pharmacy, will be evaluated by the pharmacy, and processed. The pharmacy then prepares the medication according to the requirements of the physician. Typically, the pharmacy packages the medication in a container, and a copy of the order, or at a minimum the patient's name, the drug name, and the appropriate treatment parameters are represented on an RFID transponder 50 or other data transmitting device that is affixed to the drug container.

However, in cases where the prescription is processed and/or prepared at the nurse's station rather than the pharmacy, the prescription RFID tag would be prepared at the nurse's station. If it is not already affixed to the medical container, the nurse would attach it to the fluid container received from the pharmacy or prepared by the nurse. In such cases, the fluid container may include two RFID tags, a first RFID tag from the pharmacy for identifying the drug and concentration and a second prescription RFID tag created at the nurse's station for identifying the patient, the drug prescribed, relevant infusion parameters, the physician's name, and any other relevant information desired. In another embodiment, the first RFID tag from the pharmacy may be a writable tag, in which case a nurse may program the additional prescription information on to that tag when preparing the prescription. If the prescription RFID tag is prepared at the nurse's station in response to a physician's verbal orders, for example, that tag would also include the nurse's name, badge number, and information concerning the physician and the physician's verbal orders.

Generally, the medication is then delivered to the appropriate care-giving unit for administering to the patient. A nurse or technician carries the medical fluid container 40 to the appropriate patient 48. The nurse begins by hanging the container 40 of medical fluid from a stand, such as the roller stand 46 shown in FIG. 1, priming the conduit 66 of a fluid administration set 32 with the fluid from the fluid container 40 to be infused into the patient 48, and loading the conduit 66 into the pump 24. The transponder 50 for the medical fluid container 40 transmits RFID signals through the conduit 66 via the fluid, and the signals are received by RFID reader 80 at the upstream end of the infusion pump 24. The received signals may represent information including infusion parameters that may be used to program the pump 24 automatically. This information may also be displayed on displays 55 or 62 (FIG. 2).

At the bedside, a vascular access device ("VAD") is typically placed in the patient's vascular system or body space (epidural, intrathecal, subarachnoid, etc.). Once the VAD has been connected to the primed administration set 32, the RFID signals from the patient transponder 92 travel through the medical fluid in the conduit 66 and are detected by the RFID reader 82 at the downstream end of the infusion pump 24. The data transmitted from both the fluid container transponder 50 and the patient transponder 92 are compared to verify whether the patient identification data matches. In case of a mismatch, the pump 24 alerts the caregiver and prevents fluid delivery fluid from commencing. If the patient identification data matches, the correct connection of the fluid container 40 to the patient 48 has been verified. The system thus provides for relatively automatic identification and processing to determine if the right drug is being administered to the right patient.

In addition, patient characteristics and/or the patient's MAR may also be stored in and transmitted by the patient transponder 92. The medical administration system 20 may include a drug library having medication administration guidelines including protocols and limits providing ranges of acceptable values for infusion parameters. Such guidelines may utilize the patient characteristics received from the patient transponder 92. If the system detects an out-of-range value for a parameter, the pump provides an appropriate alert to the caregiver.

Once the infusion pump 24 or other medical administration device is configured, the nurse, caregiver, or technician starts the infusion by pressing the appropriate control on the infusion pump 24 (FIG. 4). In embodiments where the patient transponder is writable, information about the infusion may then be transmitted from the pump 24 and written onto the patient transponder 92 to provide an updated MAR.

From the foregoing, it will be appreciated that the system and method in accordance with the principles of the invention provide effective means to verify that a fluid container is correctly connected to an infusion pump in order to ensure infusion of the proper drug to the patient. The interconnection between the fluid container and the infusion pump, and between the patient and the infusion pump, results in a complete communication system designed to further reduce the occurrence of medication errors and provide further patient safety as well as make the infusion process easier and more efficient for healthcare workers.

In the above detailed description, well-known devices, methods, procedures, and individual components have not been described in detail so as not to obscure aspects of the present invention. Those skilled in the art will understand those devices, methods, procedures, and individual components without further details being provided here. Moreover, while the embodiments disclosed above are described for use in a hospital environment, it will be understood that the system and method may be useful in other environments as well, such as outpatient clinics and other environments where care is delivered to a patient.

While several specific embodiments of the invention have been illustrated and described, it will be apparent that various modifications can be made without departing from the spirit and scope of the invention. Accordingly, it is not intended that the invention be limited, except as by the appended claims.

What is claimed is:

1. An infusion pump comprising:
   a body;
   a peristaltic pumping mechanism coupled to the body and comprising a plurality of fingers, the pumping mechanism configured to accept a tube of an intravenous (IV) set that is connected between a fluid container and a patient and always have at least one finger occluding the tube, wherein the tube contains a fluid from the fluid container; and
   a data reader device coupled to the body and configured to operatively couple to the tube of the IV set when the IV set is operatively engaged with the infusion pump, the data reader device configured to receive at least one radio frequency (RF) signal that is being transmitted through the fluid in the tube.

2. The infusion pump of claim 1, wherein the at least one RF signal comprises an RF signal transmitted by a RF transponder associated with the fluid container.

3. The infusion pump of claim 2, wherein the RF transponder comprises a Radio Frequency Identification (RFID) tag.

4. The infusion pump of claim 1, wherein the at least one RF signal comprises a patient identifier.

5. The infusion pump of claim 1, wherein the at least one RF signal comprises a drug identifier.

6. The infusion pump of claim 5, wherein the at least one RF signal further comprises a drug concentration.

7. The infusion pump of claim 1, wherein the data reader device comprises a capacitive coupling device configured to improve the coupling of the data reader device to the fluid within the tube.

8. The infusion pump of claim 7, wherein the capacitive coupling device comprises a metalized half-pipe.

9. An intravenous (IV) set for use with an infusion pump and a fluid container containing a medical fluid, the IV set comprising:
   a fluid tube comprising an electrically conductive substance configured to improve, compared to a fluid tube without the electrically conductive substance, the radio frequency (RF) coupling between a RF transponder associated with the fluid container and a data reader device that is operatively coupled to the tube when the IV set is operatively engaged with the infusion pump.

10. The IV set of claim 9, wherein the electrically conductive substance is embedded in at least a portion of the tube.

11. The IV set of claim 9, wherein the electrically conductive substance comprises at least a partial coating on the tube.

12. The IV set of claim 9, wherein the electrically conductive substance comprises carbon.

13. The IV set of claim 9, wherein the electrically conductive substance provides a data signal conducting pathway between the RF transponder and the data reader device that is separate from the medical fluid from the fluid container that is provided in the tube when the IV set is coupled to the fluid container.

14. The IV set of claim 9, wherein the fluid tube comprising the electrically conductive substance is configured to improve the RF coupling between at least one of the RF transponder and the data reader device and a medical fluid within the tube that is provided when the IV set is coupled to the fluid container.

15. An infusion data communication system comprising:
an intravenous (IV) set comprising:
a tube configured to couple to a fluid container at an upstream end and to a patient at a downstream end; and
an electrically conductive substance that is coupled to the tube, the conductive substance configured to provide a data signal conducting pathway between the upstream and downstream ends of the tube;
a first data transmitting device located at either the upstream end or the downstream end, the first data transmitting device configured to provide a first signal comprising relevant first administration data into the electrically conductive substance; and
a first data reader device operatively engaged with the electrically conductive substance at a position between the upstream end and the downstream end, the first data reader device configured to receive the first signal from the electrically conductive substance.

16. The infusion data communication system of claim 15, further comprising:
a second data transmitting device located at the other of the upstream end or the downstream end, the second data transmitting device configured to provide a second signal comprising second administration data into the electrically conductive substance; and
a second data reader device operatively engaged with the electrically conductive substance at a position between the upstream end and the downstream end, the second data reader device configured to receive the second signal from the electrically conductive substance.

* * * * *